United States Patent [19]
Kawamura et al.

[11] 4,033,170
[45] July 5, 1977

[54] APPARATUS FOR MOUNTING EXHAUST GAS SENSOR

[75] Inventors: Yoshihisa Kawamura; Masaaki Saito; Hidehiro Minami, all of Yokohama, Japan

[73] Assignee: Nissan Motor Co., Ltd., Yokohama, Japan

[22] Filed: Oct. 29, 1975

[21] Appl. No.: 626,831

[30] Foreign Application Priority Data
Nov. 1, 1974 Japan .................. 49132673[U]
Dec. 29, 1974 Japan .................. 50-3432[U]

[52] U.S. Cl. .................. 73/23; 123/119 E
[51] Int. Cl.² .................. G01N 27/46; G01N 31/00
[58] Field of Search .................. 73/23; 60/276, 320; 123/119 E

[56] References Cited
UNITED STATES PATENTS

| 3,616,274 | 10/1971 | Eddy | 60/276 X |
| 3,835,012 | 9/1974 | Hemak | 123/119 E X |
| 3,933,028 | 1/1976 | Laud et al. | 73/23 |

Primary Examiner—James J. Gill

[57] ABSTRACT

Herein disclosed is an apparatus by which an exhaust gas sensor is placed in flow communication with the exhaust gases issued from an engine. The apparatus is so constructed and arranged such that a volume of air is maintained about a body portion of the exhaust gas sensor in heat conductive relation with the exhaust gases. The apparatus may be provided with a heater around a probe portion of the exhaust gas sensor which projects into the exhaust conduit. The heater is selectively energized to heat the probe portion when the temperature of the exhaust gases is low.

15 Claims, 9 Drawing Figures

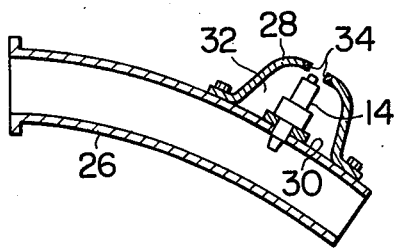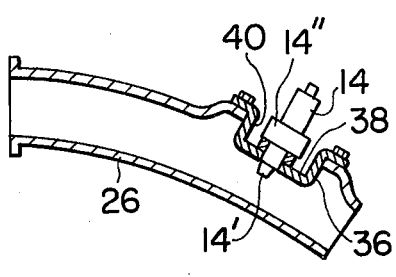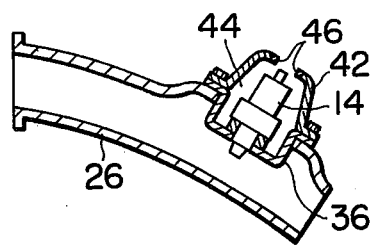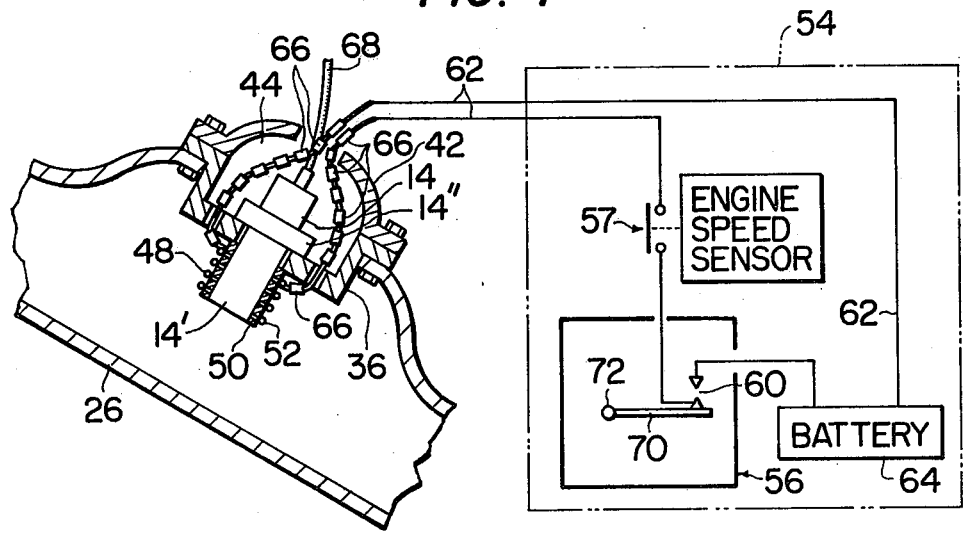

APPARATUS FOR MOUNTING EXHAUST GAS SENSOR

The present invention relates to an engine system wherein fuel and air are admixed and combusted in an engine and the resulting exhaust gases issuing therefrom. More particularly, the present invention relates to an engine system of the above character wherein air fuel ratio is controlled near the stoichiometry based on a sensor voltage from an exhaust gas sensor placed in flow communication with the exhaust gases.

In connection with the problem of reducing air pollution resulting from an automobile internal combustion engine, it is known that if the air fuel ratio (A/F) of an air-fuel mixture being applied to the engine is maintained at or near the stoichiometric, exhaust gases will contain less harmful components, i.e. hydrocarbons (HC), carbon monoxide (CO) and oxides of nitrogen ($NO_x$). It is also known that there can be a highly efficient conversion of these harmful components in a catalytic converter if the air fuel ratio is near the stoichiometry.

A conventional engine system employs an exhaust gas sensor, such as oxygen sensor which generates an electrical voltage in response to the concentration of an oxygen in exhaust gases issued from an engine. In the engine system air fuel ratio of an air-fuel mixture being applied to the engine is varied in response to the sensor voltage. One problem in this engine system stems from the fact that the sensor voltage is temperature dependent, that is, when the exhaust gas temperature is excessively low, the sensor voltage versus air fuel ratio curve shifts to the richer side. The problem is that air-fuel mixture supplied to the engine is controlled to a fixed ratio which is deviated on the richer side from the stoichiometry and becomes richer when the exhaust gas temperature is excessively low. The decrease in temperature around the oxygen sensor results in the reduction in conversion efficiency of catalysts in the catalytic converter installed in the exhaust system. Thus there is the need to compensate for the deviation from the stoichiometry.

It is a main object of the present invention to provide an engine system in which reduction of temperature about an exhaust gas sensor is prevented.

It is a specific object of the present invention to provide an engine system in which temperature of exhaust gases issued from an internal combustion engine is effectively employed as a heat source for heating a volume of air about an exhaust gas sensor.

It is another specific object of the present invention to provide an engine system in which an exhaust gas sensor is warmed up above appropriate temperature throughout all engine operating conditions of an internal combustion engine.

These and other objects, features and advantages of the present invention will become more apparent from the following description in connection with the accompanying drawings, in which:

FIGS. 4 and 6 are similar views to FIG. 2 and show embodiments in accordance with the present invention.

FIG. 7 is a similar view to FIG. 6 and shows another embodiment in accordance of the present invention.

Figure 1:
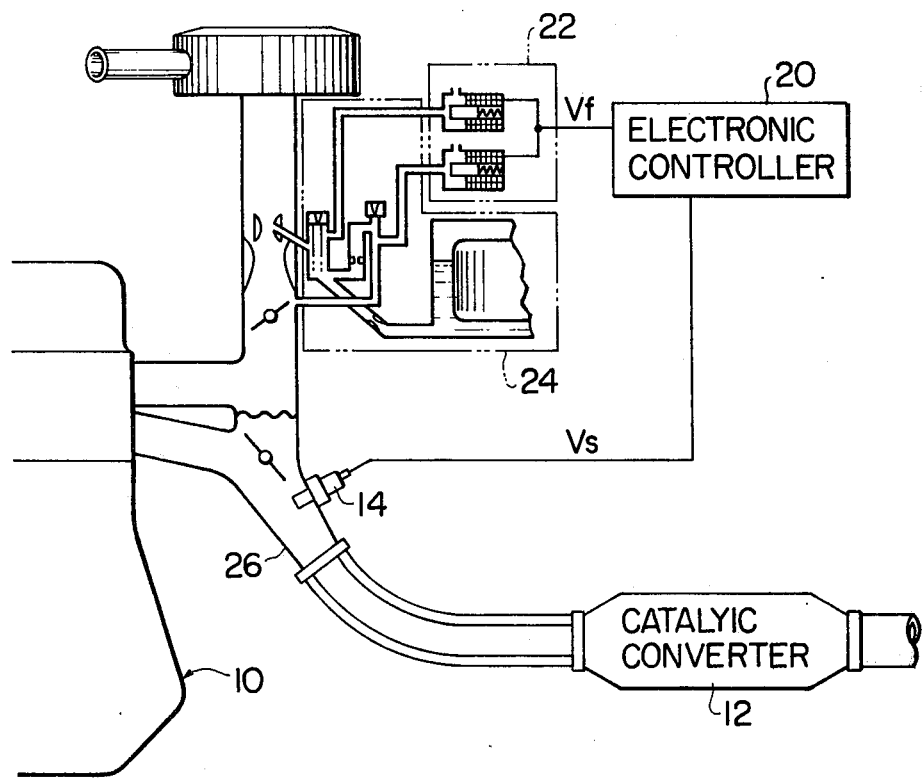
FIG. 1 is a schematic diagram showing an engine system in which an air fuel ratio of an air-fuel mixture being applied to an internal combustion engine is controlled based on an oxygen sensor placed in flow communication with exhaust gases issued from the engine.
Figure 3:
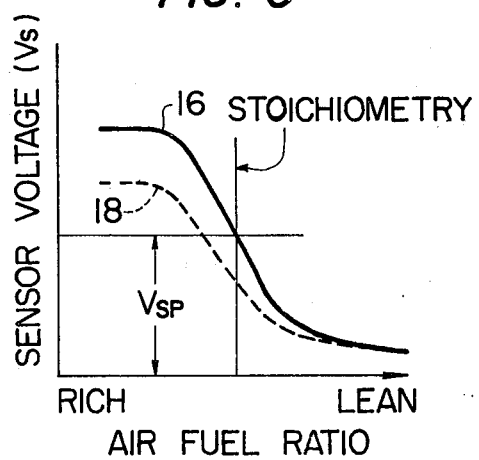
FIG. 3 is a general diagram showing changes in sensor voltage from the oxygen sensor.
Figure 9:
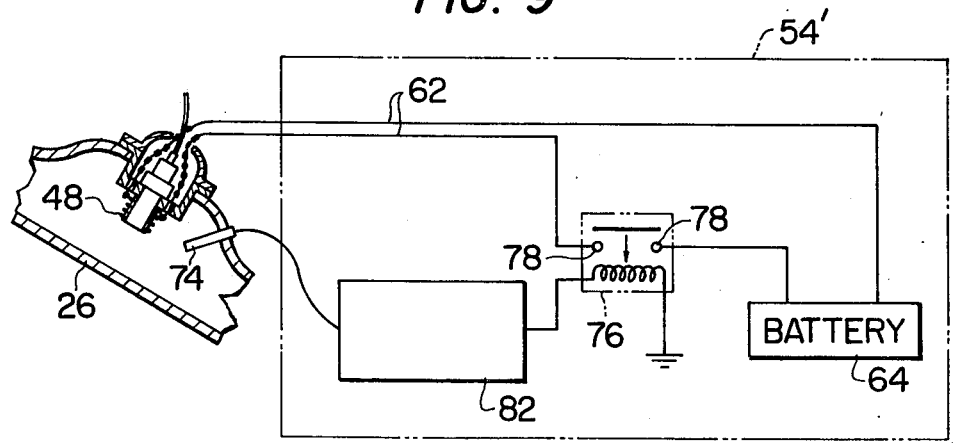

FIG. 9 is a similar view to FIG. 7 and shows still another embodiment in accordance with the present invention. FIG. 1 shows a block diagram of a conventional engine system in which the reference numeral 10 designates an internal combustion with an exhaust pipe having a three-way catalytic converter 12 placed in flow communication with exhaust gases issuing from the engine 10. The engine system includes an oxygen sensor 14 so constructed as to provide a voltage Vs in response to concentration of oxygen contained in the exhaust gases. The sensor voltage Vs of the sensor 14 is related to air fuel ratio of an air fuel mixture supplied to the engine 10. Step change in the sensor voltage Vs occurs near stoichiometry as shown by a solid curve 16 in FIG. 3. In FIG. 3 the solid curve 15 shows the change in the sensor voltage Vs when temperature of exhaust gases is higher than a temperature band ranging from 500° C to 600° C, whereas a dashed curve 18 the change in the sensor voltage Vs when temperature of exhaust gases is lower than this temperature band. Based on this sensor voltage Vs an electronic controller 20 provides an electronic feedback signal Vf to an actuator 22 which controls an air-fuel metering system 24 in such a manner that when the sensor voltage Vs is higher than a present voltage Vsp (See FIG. 3), air fuel ratio decreases and that when the sensor voltage Vs is lower than the preset voltage Vsp, air fuel ratio increases. Usually this preset voltage Vsp has a fixed magnitude so that the deviation in the sensor voltage from this fixed magnitude means deviation from the stoichiometry. Thus a problem occurs when the temperature of exhaust gases is lower than the temperature band from 500° C to 600° C since the characteristic curve changes gradually from the curve 16 to the curve 18 in response to the variation of the exhaust temperature. Thus with the sensor 14, precise control of air fuel ratio near the stoichiometry is impossible when the temperature of exhaust gases is lower than the temperature band.

Figure 2:
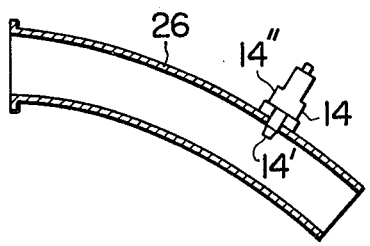
FIG. 2 is a fragmentary enlarged view of FIG. 1 and shows a prior art technique to install the oxygen sensor.

FIG. 2 is an enlarged view of FIG. 1 and shows a prior art technique of attaching the sensor 14 to an exhaust conduit 26 through which the exhaust gases flow. According to this prior art technique the sensor 14 is threadedly engaged with the exhaust conduit 26 withe its probe portion 14' projecting into the interior of the exhaust conduit 26 so that the probe portion is in flow communication with the exhaust gases. With this prior art a body portion 14" of the sensor 14 is exposed to the ambient atmosphere so that heat of the sensor 14 is deprived of by the ambient flow of air.

It will be noted that the aforementioned problem may be solved to a certain degree by keeping the sensor 14 warm.

FIG. 4 illustrates a portion of an exhaust conduit 26 to which an oxygen sensor 14 is threadedly attached in the same manner as described with reference to FIG. 2. A bell-shaped cap member 28 is secured to the exhaust conduit 26 to cover the sensor 14. The cap member 28 defines a wall 30 around the sensor 14 and the cap member 28 and the wall 30 cooperate to form a substantially closed chamber 32 about the sensor 14 so that a volume of air is maintained about the sensor 14. The wall 30 which is integral with the exhaust conduit 26 to form a part thereof is heated by the exhaust gases in the exhaust conduit 26 and serves as a heat source of the air maintained within the chamber 32. The cap member 28 has an opening at the top thereof for allowing lead lines (not shown) from the sensor 14 to pass through and is provided with an insulator defining the opening for the prevention of grounding of the lead lines.

FIG. 5 illustrates another configuration to attach an oxygen sensor 14 to an exhaust conduit 26. A cup-shaped socket 36 is secured to the exhaust conduit 26 in such a manner that the bottom wall 38 of the cup-shape projecting into the exhaust conduit 26. The sensor 14 is threadedly attached to the bottom wall 38 so that a probe portion 14' of the sensor 14 projects into the exhaust conduit 26 and a body portion or transducer portion 14" of the sensor 14 is surrounded by a side wall 40 of the socket 36. It will be noted that the socket 36 forms a well around the sensor 14 and a volume of air is maintained in the well. The bottom and side walls 38 and 40 which are heated by the exhaust gases serves as a heat source of the air within the well. It will be understood that the deeper the cup-shape of the socket 36 the more the temperature within the well increases. However there is a limit to increasing the depth of the socket 36, so that it is preferable to use a bell-shaped cap member 42 in cooperation with a cup-shaped socket 36 as illustrated in FIG. 6.

Referring to FIG. 6 the bell-shaped cap member 42 is screwed to the socket 36 to cover an oxygen sensor 14 threadedly attached to the socket 36 in the same manner as in FIG. 5. The bell-shaped cap member 42 and the cup-shaped socket 36 cooperate to form a substantially closed chamber 44 about the sensor 14. The cap member 42 has an opening at the top thereof and an insulator 46 to define the opening for the prevention of grounding of lead lines (not shown) passing through the opening. As will be understood from the comparison of the configuration shown in FIG. 6 with that shown in FIG. 5, the configuration in FIG. 6 can keep the sensor 14 warm more effectively due to the use of the bell-shaped cap member 42 in addition to the cup-shaped socket 36. Preferably the chamber 44 may be filled with an insulator to increase thermal capacity of this chamber.

In the preceding description with reference to FIGS. 4 through 6 a few kinds of configurations are shown which employ the exhaust gases as a heat source and which increase thermal capacity about the sensor in order to keep the oxygen sensor warm. The use of exhaust gas as a heat source has the shortcoming that the exhaust gases will not work as the heat source when the temperature of the exhaust gases is low. To overcome or compensate for this shortcoming it is proposed to elevate temperature about the sensor 14 when the temperature of exhaust gases is low. This will now be described with reference to FIGS. 7 and 8.

Figure 8:
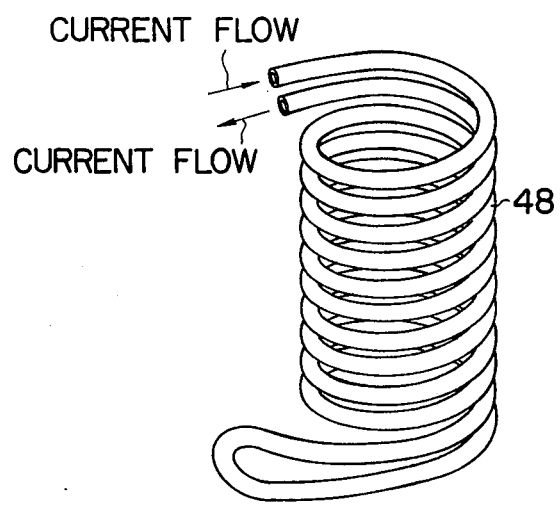
FIG. 8 is a perspective view showing a heater coil used in FIG. 7.

FIG. 7 illustrates a similar view to FIG. 6 so tht like reference numerals are used to designate like parts and description of the like parts is omitted for the sake of simplicity. However the difference resides in that around a proble portion 14' of an oxygen sensor 14 a coiled heater 48 (see also FIG. 8) is provided to heat the probe portion 14' when current flows through the coiled heater 48 in the directions as indicated by arrows in FIG. 8. A cylindrical insulator member 50 made of a ceramics covers the probe portion 14' and is provided with a plurality of apertures only one being designated at 52. Through the apertures 52 the probe portion 14' is in flow communication with the exhaust gases flowing through an exhaust conduit 26. The coiled heater 48 surrounds the insulator member 50. As best shown in FIG. 8 the heater 48 should be so constructed as to the noninductive and such that there will be no effect of current flowing through the coiled heater 48 on the probe portion 14' of the sensor 14.

To selectively energize the heater 48 an electric control circit 54 is provided. The control circuit 54 includes a condition responsive switch 56 having a pair of contact 60 which are circulated in seris with the coiled heater 50 through lead lines 62 and with a battery 64. A plurality of insulators 66 cover the lead lines 62 so as to prevent grounding of the lead lines 62. Designated by 68 is a lead line by whih sensor output is applied to the electronic controller 20 (see FIG. 1). The switch 56 includes a wiper arm 70 having one of the contacts 60 thereon. The wiper arm 70 has one end coupled with a spindle 72 on which a throttle flap (not shown) is mounted in such a manner that the contacts 60 are closed when the throttle flap is substantially closed, that is when the engine is idling. Alternatively the switch 56 may be operatively connected to an accelerator pedal (not shown) for the control of the throttle flap or may be operated manually in such a manner that the contacts 60 are closed during engine operating condition in which temperature in the exhaust gases issuing from the engine is low.

It will now be noted that the control circuit 54 is so constructed and arranged such that the coiled heater 48 is energized when the temperature is exhaust gases is low by detecting such engine operating condition which causes exhaust gas temperature reduction.

If the idle speed condition is to be detected, an engine speed responsive switch 57 is circuited in series with the switch 56. The switch 57 is closed when the engine speed (rpm) is at idle speed.

FIG. 9 illustrates a similar view to FIG. 7 so that the like parts throughout these two Figures are designated by like reference numerals. To directly sense the temperature in the exhaust gases flowing through an exhaust conduit 26 a temperature sensor 74 projects into the exhaust conduit 26, the temperature sensor 74 being of the type that output voltage signal from the temperature sensor 74 is representative of the temperature of the exhaust gases detected in the exhaust conduit 26. An electric control circuit for energizing a coiled heater 48 is now indicated by 54' and includes a temperature responsive switch 76 having a pair of normally open contacts 78 connected in series with the coiled heater 48 and a battery 64 through lead lines 62. The switch 776 further includes a relay coil 80 which when energized causes the contacts 78 to be closed. The relay coil is so circuited through a computer circuit with the output of the temperature sensor that when the temperature of the exhaust gases is lower than a predetermined value the relay coil 80 is energized and the associated contacts 78 are closed.

As described in the preceding the effect of drop in temperature of the exhaust gases on the sensor output of the oxygen sensor 14 is reduced to a minimum in accordance with the present invention. Thus precise control of air fuel ratio near stoichiometry in the engine system as schematically illustrated in FIG. 1 is possible in accordance with the present invention.

1. An engine system comprising:
   an exhaust conduit through which exhaust gases issuing from the engine flow;
   an exhaust gas sensor placed in flow communication with the exhaust gases in such a manner that a probe portion of the exhaust gas sensor is exposed to the flow of exhaust gases;
   an insulator member covering the probe portion, the insulator member being provided with a plurality of apertures by which the probe portion is in flow communication with the exhaust gases;
   a coiled heater surrounding the insulator member;
   a pair of contacts circuited in series with the coiled heater;
   means for sensing idling of the engine; and means for closing the pair of contacts in response to said sensing means.

2. An engine system as claimed in claim 1, in which the closing means includes
   a mechanism operatively connected to a throttle flap of the engine to close the pair of contact when the throttle flap is closed.

3. An engine system as claimed in claim 1, in which the closing means includes.
   a mechanism operatively connected to an accelerator pedal of the engine to close the pair of contacts when the accelerator pedal is released.

4. An engine system comprising:
   an exhaust conduit through which exhaust gases issuing from the engine flow;
   first means having a wall portion that forms a part of the exhaust conduit, the wall portion contacting with the exhaust gases;
   an exhaust gas sensor secured to the wall portion with a probe portion exposed to the exhaust gases flowing through the exhaust conduit;
   an insulator member covering the probe portion, the insulator member being provided with a plurality of apertures by which the probe portion is in flow communication with the exhaust gases;
   a coiled heater surrounding the insulator member;
   a pair of contact circuited in series with the coiled heater; and
   means for closing the pair of contacts in response to a predetermined operating condition of the engine,
   in which said first means includes a cap member covering a remaining portion of the exhaust gas sensor, the cap member and the wall portion cooperating to form a substantially closed member around the remaining portion of the exhaust gas sensor.

5. An engine system as claimed in claim 4, in which an insulator fills the closed chamber.

6. An engine system as claimed in claim 4, in combination with the first means of an insulator filling the closed chamber.

7. An engine system comprising:
   an exhaust conduit through which exhaust gases issuing from the engine flow;
   first means having a wall portion that forms a part of the exhaust conduit, the wall portion contacting with the exhaust gases;
   an exhaust gas sensor secured to the wall portion with a probe portion exposed to the exhaust gases flowing through the exhaust conduit;
   an insulator member covering the probe portion, the insulator member being provided with a plurality of apertures by which the probe portion is in flow communication with the exhaust gases;
   a coiled heater surrounding the insulator member;
   a pair of contacts circuited in series with the coiled heater; and
   means for closing the pair of contacts in response to a predetermined operating condition of the engine,
   in which the wall portion projects into the exhaust conduit to form a well around the remaining portion of the exhaust gas sensor.

8. An engine system comprising;
   an exhaust conduit through which exhaust gases issuing from the engine flow;
   first means having a wall portion that forms a part of the exhaust conduit, the wall portion contacting with the exhaust gases;
   an exhaust gas sensor secured to the wall portion with a probe portion exposed to the exhaust gases flowing through the exhaust conduit;
   an insulator member covering the probe portion, the insulator member being provided with a plurality of apertures by which the probe portion is in flow communication with the exhaust gases;
   a coiled heater surrounding the insulator member;
   a pair of contacts circuited in series with the coiled heater; and
   means for closing the pair of contacts in response to a predetermined operating condition of the engine,
   in which the wall portion projects into the exhaust conduit to form a well around the remaining portion of the exhaust gas sensor and in which the first means includes a cap member covering the remaining portion of the exhaust gas sensor, the cap member and the wall portion cooperating to form a substantially closed chamber including the well around the remaining portion of the exhaust gas sensor.

9. An engine system as claimed in claim 8, in which an insulator fills the closed chamber.

10. An engine system as claimed in claim 8, in combination with the first means of an insulator filling the closed chamber.

11. An engine system comprising:
    an exhaust conduit through which exhaust gases issuing from the engine flow;
    an exhaust gas sensor placed in flow communication with the exhaust gases in such a manner that a probe portion of the exhaust gas sensor is exposed to the flow of exhaust gases;
    an insulator member covering the probe portion, the insulator member being provided with a plurality of apertures by which the probe portion is in flow communication with the exahaust gases;
    a coiled heater surrounding the insulator member;
    a pair of contacts cicuited in series with the coiled heater; and
    means for closing the pair of contacts in response to a pedetermined operating condition of the engine
    said closing means including a mechanism operatively connected to a throttle flap of the engine to close the pair of contacts when the throttle flap is closed.

12. An engine system comprising:
    an exhaust conduit through which exhaust gases issuing from the engine flow;

an exhaust gas sensor placed in flow communication with the exhaust gases in such a manner that a probe portion of the exhaust gas sensor is exposed to the flow of exhaust gases;

an insulator member covering the probe portion, the insulator member being provided with a plurality of apertures by which the probe portion is in flow communication with the exhaust gases;

a coiled heater surrounding the insulator member;

a pair of contacts circuited in series with the coiled heater; and means for closing the pair of contacts in response to a predetermined operating condition of the engine, said closing means including a mechanism operatively connected to an accelerator pedal of the engine to close the pair of contacts when the accelerator pedal is released.

13. An engine system comprising:

an exhaust conduit through which exhaust gases issuing from the engine flow;

an exhaust gas sensor placed in flow communication with the exhaust gases in such a manner that a probe portion of the exhaust gas sensor is exposed to the flow of exhaust gases;

an insulator member covering the probe portion, the insulator member being provided with a plurality of apertures by which the probe portion is in flow communication with the exhaust gases;

a coiled heater surrounding the insulator member;

a pair of contacts circuited in series with the coiled heater; means for sensing coasting of the engine; and means for closing the pair of contact in response to said sensing means.

14. An engine system as claimed in claim 13, in which the closing means includes a mechanism operatively connected to a throttle flap of the engine to close the pair of contacts when the throttle flap is closed.

15. An engine system as claimed in claim 13 in which the closing means includes a mechanism operatively connected to an accelerator pedal of the engine to close the pair of contact when the accelerator pedal is released.

* * * * *